US006831059B2

(12) United States Patent
Donovan

(10) Patent No.: US 6,831,059 B2

(45) Date of Patent: Dec. 14, 2004

(54) COMPOSITIONS AND METHODS FOR TREATING GONADOTROPHIN RELATED ILLNESSES

(75) Inventor: Stephen Donovan, Capistrano Beach, CA (US)

(73) Assignee: Allergan, Inc., Irvine, CA (US)

( * ) Notice: Subject to any disclaimer, the term of this patent is extended or adjusted under 35 U.S.C. 154(b) by 105 days.

(21) Appl. No.: 09/810,601

(22) Filed: Mar. 15, 2001

(65) Prior Publication Data

US 2002/0177545 A1 Nov. 28, 2002

Related U.S. Application Data

(63) Continuation-in-part of application No. 09/692,811, filed on Oct. 20, 2000.

(51) Int. Cl.[7] .......... A61K 38/00; A61K 49/00; A61K 39/08

(52) U.S. Cl. .......... 514/2; 514/12; 530/350; 424/9.1; 424/239.1; 424/195.11; 435/69.7; 435/320.1

(58) Field of Search .......... 514/2, 12, 15; 530/350, 412; 435/69.7, 320.1, 69.1, 325, 252.3; 424/239.1, 195.11, 9.1; 536/23.1

(56) References Cited

U.S. PATENT DOCUMENTS

| | | | |
|---|---|---|---|
| 5,378,688 A | 1/1995 | Nett et al. | |
| 5,459,127 A | 10/1995 | Felgner et al. | |
| 5,631,229 A | 5/1997 | Nett et al. | |
| 5,707,964 A | 1/1998 | Nett et al. | |
| 5,939,070 A | 8/1999 | Johnson et al. | |
| 5,989,545 A | 11/1999 | Foster et al. | |
| 6,005,086 A | 12/1999 | Evans et al. | |
| 6,139,845 A | 10/2000 | Donovan | 424/236.1 |
| 6,395,513 B1 | 5/2002 | Foster et al. | |
| 6,461,617 B1 | 10/2002 | Shone et al. | |

FOREIGN PATENT DOCUMENTS

| | | | |
|---|---|---|---|
| WO | WO 90/09799 | 9/1990 | |
| WO | WO 96/33273 | 10/1996 | |
| WO | WO 98/07864 | 2/1998 | |
| WO | WO 99/17806 | 4/1999 | |
| WO | WO 00/57897 | 10/2000 | |
| WO | WO 02/34286 A1 | 5/2002 | A61K/38/48 |

OTHER PUBLICATIONS

U.S. patent application Ser. No. 09/692,811, Donovan, filed Oct. 20, 2000.

U.S. patent application Ser. No. 09/288,326, Aoki et al., filed Apr. 8, 1999.

U.S. patent application Ser. No. 09/620,840, Steward et al., filed Jul. 21, 2000.

"Immunohistochemical Study of Syntain–1 and Snap–25 in The Pituitaries of Mouse, Guinea Pig and Cat", E. Salinas et al. APPTLA 49, pp. 61–64, 1999.

"Hormonal Regulation of Endometriosis and the Rationales and Effects of Gonadotrophin–Releasing Hormone Agonist Treatment: A Review", I.A. Bergqvist, Human Reproduction, vol. 10, No. 2, pp. 446–452, 1995.

(List continued on next page.)

*Primary Examiner*—Christopher S. F. Low
*Assistant Examiner*—Chih-Min Kam
(74) *Attorney, Agent, or Firm*—Stephen Donovan; Martin A. Voet; Robert J. Baran

(57) ABSTRACT

The present invention relates to an agent comprising a neurotoxin, methods for making the agents and methods for treating endocrine disorders, for example gonadotrophin related illnesses. Preferably, the agent comprises at least a portion of a *botulinum toxin.*

6 Claims, 1 Drawing Sheet

OTHER PUBLICATIONS

"Management of pituitary gonadal function via gonadotrophin releasing hormone (GnRH) antagonists, including ovulation induction by co–administration of either gonadotrophins or pulsatile GmRH" Keith Gordon et al. Human Reproduction vol. 8, Suppl2, pp 204–209, 1993.

"Targeting drugs to the brain by redox chemical delivery systems", Laszio Prokai et al., John Wiley & Sons, Inc. Med Res Rev, 20, No. 5, pp. 367–416, 2000.

"New Advances in the Transport of Doxorubicin through the Blood–Brain Barrier by a Peptide Vector–Mediated Strategy", Christophe Rousselle et al., Molecular Pharmacology, 57:679–686, 2000.

"Gonadotropin–Releasing Hormone Receptor: Gene Structure, Expression and Regulation", Peter C.K. Leung and Chun Peng. Biological Signals, 1996;5:63–69.

"Nucleotide Sequence Analysis Predict that Human Pituitary and Human Placental Gonadotropin–Releasing Hormone Receptors have Identical Primary Structures", Timothy A. Boyle et al., Endocrine, vol. 9, No. 3, 281–287, Dec. 1998.

"Transporter–Mediated Permeation of Drugs Across the Blood–Brain Barrier", Ikumi Tamai and Akira Tsuji, Journel of Pharmaceutical Sciences, vol. 89, No. 11, Nov. 2000.

"Accumulation of Synaptosomal–Associated Protein of 25kDa (SNAP–25) and Other Proteins Associated with the Secretory Pathway in GH4C1 Cells Upon Treatment with Estradiol, Insulin, and Epidermal Growth Factor", Min S. Lee et al., Endocrinology, vol. 141, No. 9, pp. 3485–3492, 2000.

"Localization and Physiological Regulation of the Exocytosis Protein SNAP–25 in the Brain and Pituitary Gland of Xenopus laeis", S.M. Kolk et al. Journal of Neuroendocrinology, 2000, vol. 12, 694–706.

"MCB 3320 Peptide Hormones" William S. Messer, Jr., http://www.neurosci.pharm.utoledo.edu/MCB3320/TRH.htm, Mar. 15, 2000.

"Senior Thesis–Introduction" http://www.sar.usf.edu/~sudberry/thesis/intro.html Dec. 11, 2000.

"Rule RB–1.1 and Tables 1 and 2–Revison of the extended Hantzsc–Widman system of nomenclature for heteromonocycles", http://www.chem.qmw.ac.uk/iupac/hetero/HW1nT.html, Dec. 26, 2000.

"Luteinizing Hormone–Releasing Hormone (LHRH) Neuronal System: From Basic to Clinical", Serge Rivest and Leonello Cusan, Laboratory of Molecular Endocrinology, pp 1–27, http://www.acnp.org/G4/GN401000058/CH058/html, Dec. 26, 2000.

Muchau, A. et al., *Uses of botulinum toxin injection in medicine today*, BMJ vol. 320, Jan. 15, 2000, pp. 161–165.

SEQUENCE LISTING

```
<160> NUMBER OF SEQ ID NOS: 52

<210> SEQ ID NO 1
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is PyroGlu

<400> SEQUENCE: 1

Xaa His Trp Ser Tyr Gly Leu Arg Pro Gly
```

-continued 1 5 10

<210> SEQ ID NO 2
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 2

Xaa His Trp Ser Tyr Gly Leu Arg Pro Xaa
1 5 10

<210> SEQ ID NO 3
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 3

Xaa His Trp Ser Tyr Gly Leu Arg Xaa
1 5

<210> SEQ ID NO 4
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 4

Xaa His Trp Ser Tyr Gly Leu Arg Pro Xaa
1 5 10

<210> SEQ ID NO 5
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)

-continued

```
<223> OTHER INFORMATION: Xaa at position 10 is Gly-NH2

<400> SEQUENCE: 5

Xaa His Trp Ser Tyr Lys Leu Arg Pro Xaa
1               5                   10


<210> SEQ ID NO 6
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 6

Xaa His Trp Ser Tyr Lys Leu Arg Xaa
1               5


<210> SEQ ID NO 7
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 7

Xaa His Trp Ser Tyr Lys Leu Arg Pro Xaa
1               5                   10


<210> SEQ ID NO 8
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Lys
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 8

Xaa His Trp Ser Tyr Xaa Leu Arg Pro Xaa
1               5                   10


<210> SEQ ID NO 9
<211> LENGTH: 9
<212> TYPE: PRT
<213> ORGANISM: Artificial Sequence
```

-continued

```
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Lys
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 9

Xaa His Trp Ser Tyr Xaa Leu Arg Xaa
1               5


<210> SEQ ID NO 10
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Lys
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 10

Xaa His Trp Ser Tyr Xaa Leu Arg Pro Xaa
1               5                   10


<210> SEQ ID NO 11
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is Ornithine
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 11

Xaa His Trp Ser Tyr Xaa Leu Arg Pro Xaa
1               5                   10


<210> SEQ ID NO 12
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
```

-continued

<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is Ornithine
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 12

Xaa His Trp Ser Tyr Xaa Leu Arg Xaa
1 5

<210> SEQ ID NO 13
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is Ornithine
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 13

Xaa His Trp Ser Tyr Xaa Leu Arg Pro Xaa
1 5 10

<210> SEQ ID NO 14
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-ornithine
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 14

Xaa His Trp Ser Tyr Xaa Leu Arg Pro Xaa
1 5 10

<210> SEQ ID NO 15
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE -continued
<222> LOCATION: (6)..(6)
<223> OTHER INFORMATION: Xaa at position 6 is D-Ornithine
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 15

Xaa His Trp Ser Tyr Xaa Leu Arg Xaa
1 5

<210> SEQ ID NO 16
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Ornithine
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 16

Xaa His Trp Ser Tyr Xaa Leu Arg Pro Xaa
1 5 10

<210> SEQ ID NO 17
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 17

Xaa His Trp Ser Tyr Glu Leu Arg Pro Xaa
1 5 10

<210> SEQ ID NO 18
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 18

Xaa His Trp Ser Tyr Glu Leu Arg Xaa
1 5

-continued

```
<210> SEQ ID NO 19
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 19

Xaa His Trp Ser Tyr Glu Leu Arg Pro Xaa
1               5                   10


<210> SEQ ID NO 20
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Glu
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 20

Xaa His Trp Ser Tyr Xaa Leu Arg Pro Xaa
1               5                   10


<210> SEQ ID NO 21
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Glu
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 21

Xaa His Trp Ser Tyr Xaa Leu Arg Xaa
1               5


<210> SEQ ID NO 22
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
```

-continued

```
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Glu
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 22

Xaa His Trp Ser Tyr Xaa Leu Arg Pro Xaa
1               5                   10


<210> SEQ ID NO 23
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 23

Xaa His Trp Ser Tyr Asp Leu Arg Pro Xaa
1               5                   10


<210> SEQ ID NO 24
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 24

Xaa His Trp Ser Tyr Asp Leu Arg Xaa
1               5


<210> SEQ ID NO 25
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 25

Xaa His Trp Ser Tyr Asp Leu Arg Pro Xaa
1               5                   10
```

-continued

<210> SEQ ID NO 26
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Asp
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 26

```
Xaa His Trp Ser Tyr Xaa Leu Arg Pro Xaa
1               5                   10
```

<210> SEQ ID NO 27
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Asp
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 27

```
Xaa His Trp Ser Tyr Xaa Leu Arg Xaa
1               5
```

<210> SEQ ID NO 28
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Asp
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 28

```
Xaa His Trp Ser Tyr Xaa Leu Arg Pro Xaa
1               5                   10
```

<210> SEQ ID NO 29
<211> LENGTH: 10

-continued

```
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 29

Xaa His Trp Ser Tyr Cys Leu Arg Pro Xaa
1               5                   10


<210> SEQ ID NO 30
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 30

Xaa His Trp Ser Tyr Cys Leu Arg Xaa
1               5


<210> SEQ ID NO 31
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 31

Xaa His Trp Ser Tyr Cys Leu Arg Pro Xaa
1               5                   10


<210> SEQ ID NO 32
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Cys
<220> FEATURE:
<221> NAME/KEY: MISC_FEATURE
<222> LOCATION: (10)..(10)
<223> OTHER INFORMATION: Xaa at position 10 is Gly-NH2
```

-continued

<400> SEQUENCE: 32

Xaa His Trp Ser Tyr Xaa Leu Arg Pro Xaa
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Cys
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 33

Xaa His Trp Ser Tyr Xaa Leu Arg Xaa
1               5

<210> SEQ ID NO 34
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Cys
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 34

Xaa His Trp Ser Tyr Xaa Leu Arg Pro Xaa
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 35

Xaa His Trp Ser Tyr Tyr Leu Arg Pro Xaa
1               5                   10

<210> SEQ ID NO 36

-continued

<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 36

Xaa His Trp Ser Tyr Tyr Leu Arg Xaa
1 5

<210> SEQ ID NO 37
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 37

Xaa His Trp Ser Tyr Tyr Leu Arg Pro Xaa
1 5 10

<210> SEQ ID NO 38
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Tyr
<220> FEATURE:
<221> NAME/KEY: MISC_FEATURE
<222> LOCATION: (10)..(10)
<223> OTHER INFORMATION: Xaa at position 10 is Gly-NH2

<400> SEQUENCE: 38

Xaa His Trp Ser Tyr Xaa Leu Arg Pro Xaa
1 5 10

<210> SEQ ID NO 39
<211> LENGTH: 9
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)

-continued

<223> OTHER INFORMATION: Xaa at position 6 is D-Tyr
<220> FEATURE:
<221> NAME/KEY: MISC_FEATURE
<222> LOCATION: (9)..(9)
<223> OTHER INFORMATION: Xaa at position 9 is proline-ethylamide

<400> SEQUENCE: 39

Xaa His Trp Ser Tyr Xaa Leu Arg Xaa
1               5

<210> SEQ ID NO 40
<211> LENGTH: 10
<212> TYPE: PRT
<213> ORGANISM: Artificial Sequence
<220> FEATURE:
<223> OTHER INFORMATION: Gonadotrophin Release Hormone Analogue
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is D-Tyr
<220> FEATURE:
<221> NAME/KEY: MISC_FEATURE
<222> LOCATION: (10)..(10)
<223> OTHER INFORMATION: Xaa at position 10 is Aza-Gly-NH2

<400> SEQUENCE: 40

Xaa His Trp Ser Tyr Xaa Leu Arg Pro Xaa
1               5                   10

<210> SEQ ID NO 41
<211> LENGTH: 15
<212> TYPE: PRT
<213> ORGANISM: Human

<400> SEQUENCE: 41

Glu Pro Lys Ser Cys Asp Lys Thr His Thr Cys Pro Pro Cys Pro
1               5                   10                  15

<210> SEQ ID NO 42
<211> LENGTH: 18
<212> TYPE: PRT
<213> ORGANISM: Artificial Sequence
<220> FEATURE:
<223> OTHER INFORMATION: Membrane Translocation Peptide

<400> SEQUENCE: 42

Arg Gly Gly Arg Lys Ser Trp Ser Arg Arg Arg Phe Ser Thr Ser Thr
1               5                   10                  15

Gly Arg

<210> SEQ ID NO 43
<211> LENGTH: 23
<212> TYPE: DNA
<213> ORGANISM: Artificial Sequence
<220> FEATURE:
<223> OTHER INFORMATION: PCR DNA primer

<400> SEQUENCE: 43
aaaggccttt tgttaataaa caa                                             23

<210> SEQ ID NO 44
<211> LENGTH: 26
<212> TYPE: DNA
<213> ORGANISM: Artificial Sequence -continued
<220> FEATURE:
<223> OTHER INFORMATION: PCR DNA primer

<400> SEQUENCE: 44
ggaattctta cttattgtat ccttta 26

<210> SEQ ID NO 45
<211> LENGTH: 13
<212> TYPE: PRT
<213> ORGANISM: Artificial Sequence
<220> FEATURE:
<223> OTHER INFORMATION: Synthetic peptide

<400> SEQUENCE: 45

Cys Ala Asn Gln Arg Ala Thr Lys Met Leu Gly Ser Gly
1 5 10

<210> SEQ ID NO 46
<211> LENGTH: 9
<212> TYPE: PRT
<213> ORGANISM: Artificial Sequence
<220> FEATURE:
<223> OTHER INFORMATION: Gonadotrophin Release Hormone or Analog thereof
<220> FEATURE:
<221> NAME/KEY: MISC_FEATURE
<222> LOCATION: (1)..(1)
<223> OTHER INFORMATION: Xaa at position 1 is PyroGlu
<220> FEATURE:
<221> NAME/KEY: MISC_FEATURE
<222> LOCATION: (6)..(6)
<223> OTHER INFORMATION: Xaa at position 6 is glycine, lysine, D-lysine, ornithine, D-ornithine, glutamic acid, D-glutamic acid, aspartic acid, D-aspartic acid, cysteine, D-cysteine, tyrosine, or D-tyrosine
<220> FEATURE:
<221> NAME/KEY: MISC_FEATURE
<222> LOCATION: (9)..(9)
<223> OTHER INFORMATION: Xaa at position 9 is proline-Gly-NH2, proline-ethylamide, or proline-Aza-Gly-NH2

<400> SEQUENCE: 46

Xaa His Trp Ser Tyr Xaa Leu Arg Xaa
1 5

<210> SEQ ID NO 47
<211> LENGTH: 63
<212> TYPE: DNA
<213> ORGANISM: Artificial Sequence
<220> FEATURE:
<223> OTHER INFORMATION: DNA construct (pMAL-L)

<400> SEQUENCE: 47
atcgagggaa ggatttcaga attcggatcc tctagagtcg acatgccaat aaccataaag 60
ctt 63

<210> SEQ ID NO 48
<211> LENGTH: 19
<212> TYPE: PRT
<213> ORGANISM: Artificial Sequence
<220> FEATURE:
<223> OTHER INFORMATION: Amino acid sequence of the first several residues of the purified recombinant L chain of TeTx

<400> SEQUENCE: 48

Ile Glu Gly Arg Ile Ser Glu Phe Gly Ser Ser Arg Val Asp Met Pro
1 5 10 15

Ile Thr Ile

-continued

<210> SEQ ID NO 49
<211> LENGTH: 11
<212> TYPE: PRT
<213> ORGANISM: Artificial Sequence
<220> FEATURE:
<223> OTHER INFORMATION: Portion of the L chain of TeTx

<400> SEQUENCE: 49

Leu Leu Met His Glu Leu Ile His Val Leu His
1 5 10

<210> SEQ ID NO 50
<211> LENGTH: 5
<212> TYPE: PRT
<213> ORGANISM: Artificial Sequence
<220> FEATURE:
<223> OTHER INFORMATION: Amino acid sequence with cleavage site for bovine enterokinase

<400> SEQUENCE: 50

Asp Asp Asp Asp Lys
1 5

<210> SEQ ID NO 51
<211> LENGTH: 8
<212> TYPE: PRT
<213> ORGANISM: Artificial Sequence
<220> FEATURE:
<223> OTHER INFORMATION: Amino acid sequence with cleavage site for tobacco etch virus protease
<220> FEATURE:
<221> NAME/KEY: MISC_FEATURE
<222> LOCATION: (2)..(2)
<223> OTHER INFORMATION: Xaa at position 2 is any amino acid
<220> FEATURE:
<221> NAME/KEY: MISC_FEATURE
<222> LOCATION: (3)..(3)
<223> OTHER INFORMATION: Xaa at position 3 is any amino acid
<220> FEATURE:
<221> NAME/KEY: MISC_FEATURE
<222> LOCATION: (5)..(5)
<223> OTHER INFORMATION: Xaa at position 5 is any amino acid

<400> SEQUENCE: 51

Glu Xaa Xaa Tyr Xaa Gln Ser Gly
1 5

<210> SEQ ID NO 52
<211> LENGTH: 8
<212> TYPE: PRT
<213> ORGANISM: Artificial Sequence
<220> FEATURE:
<223> OTHER INFORMATION: Amino acid sequence with cleavage site for PRECISSION protease from human rhinovirus 3C

<400> SEQUENCE: 52

Leu Glu Val Leu Phe Gln Gly Pro
1 5

COMPOSITIONS AND METHODS FOR TREATING GONADOTROPHIN RELATED ILLNESSES

RELATED APPLICATION

The present application is a continuation-in-part of co-pending application Ser. No. 09/692,811, dated Oct. 20, 2000, the disclosure of which is hereby incorporated, in its entirety, herein by reference.

BACKGROUND OF THE INVENTION

In 1971, after years of intense research, Andrew Schally finally was able to identify the structure of the releasing hormone responsible for stimulating the secretion of luteinizing hormones (LH) and follicle-stimulating hormones (FSH) from the pituitary gland. This releasing hormone is produced by the hypothalamus and reaches the pituitary gland by a neurohumoral pathway.

Today, the importance of this releasing hormone is widely recognized for its regulatory role in human development and growth. Furthermore, this releasing hormone may be the basis of various crippling illnesses. Commonly, this particular releasing hormone is referred to as the gonadotrophin-releasing hormone (GnRH).

A normal production of GnRH beneficially regulates the body's level of LH and FSH (also known as gonadotrophins). LH together with FSH stimulates the release of estrogens from the maturing follicles in the ovary and induces the process of ovulation in the female. In the male, LH stimulates the interstitial cells and is, for that reason, also called interstitial cell stimulating hormone (ICSH). FSH induces maturation of the follicles in the ovary and together with LH, plays an important role in the cyclic phenomena in the female. FSH promotes the development of germinal cells in the testes of the male.

However, an abnormally high production of GnRH by the hypothalamus may cause an increased gonadotrophin secretion, which may deleteriously harm the body. A high level of circulating gonadotrophin is known to cause, for example, precocious puberty, endometriosis, breast cancer, prostate cancer, pancreatic cancer and endometrial cancer. These illnesses may be treated by reducing the level of gonadotrophin secretion.

GnRH agonists and antagonists are existing drugs that act to decrease gonadotrophin secretion. GnRH agonists act by initially increasing the quantity of gonadotrophin secreted by the pituitary. However, with treatment of the agonist over a period of time, gonadotrophin secretion will decrease. (Presently, the mechanism behind how the agonist reduces gonadotrophin secretion is not fully understood.)

GnRH antagonists act by binding competitively to the GnRH receptors on the pituitary thereby preventing GnRH from exerting its stimulatory effect on pituitary cells.

GnRH antagonists and agonists have proven effective in the treatment of certain conditions which require a reduction of gonadotrophin release. For example, they have proven effective in the treatment of endometriosis, uterine fibroids, polycystic ovarian disease, precocious puberty and several gonadal steroid-dependent neoplasia, most notably cancers of the prostate, breast and ovary.

GnRH agonists and antagonists have also been investigated as a potential contraceptive in both men and women. They have also shown possible utility in the treatment of pituitary gonadotroph adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus.

Although GnRH agonist and antagonist have been useful, their continual administration may be problematic. For example, treatment using GnRH agonists is normally limited to a six-month duration because of the negative effects that GnRH agonist therapy can have on bone mineral density (BMD). Women of reproductive age who undergo GnRH agonist therapy often show as much as 2.3% loss in BMD, comparable to the loss typically experienced by women in the first several years of menopause. This loss in women of reproductive age is particularly noteworthy, because bone density in women of this age group is still often increasing. Use of GnRH antagonists in the clinical setting is a relatively new event.

Nett et al. in U.S. Pat. No. 5,631,229 further discloses a potential method of reducing GnRH secretion by administering to a patient a cytotoxin conjugate, for example a diphtheria toxin-GnRH. (The disclosure of Nett et al. is incorporated in its entirety herein by reference). Although such conjugate may reduce GnRH secretion, its long-term administration may amount to a continual destruction of cells in the brain, which may be detrimental.

*Botulinum* Toxin

The bacterial genus Clostridium includes more than one hundred and twenty seven species, grouped according to morphology and function. The anaerobic, gram-positive bacterium *Clostridium botulinum* produces a potent polypeptide neurotoxin, *botulinum* toxin, which causes the neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating food infected with a *Clostridium botulinum* culture or spores. The *botulinum* toxin can apparently pass unattenuated through the lining of the gut and attack peripheral motor nerves. Symptoms of *botulinum* toxin intoxication can progress from difficulty walking, swallowing, and speaking to paralysis of the respiratory muscles and death.

*Botulinum* toxin type A is the most lethal natural biological agent known to man. About 50 picograms of a commercially available *botulinum* toxin type A (purified neurotoxin complex)[1] is a $LD_{50}$ in mice (i.e. 1 unit). One unit of BOTOX® contains about 50 picograms (about 56 attomoles) of *botulinum* toxin type A complex. Interestingly, on a molar basis, *botulinum* toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins,* pages 63–84 (chapter 4) of Natural Toxins II, edited by B. R. Singh et al., Plenum Press, New York (1976) (where the stated $LD_{50}$ of *botulinum* toxin type A of 0.3 ng equals 1 U is corrected for the fact that about 0.05 ng of BOTOX® equals 1 unit). One unit (U) of *botulinum* toxin is defined as the $LD_{50}$ upon intraperitoneal injection into female Swiss Webster mice weighing 18 to 20 grams each.

Seven generally immunologically distinct *botulinum* neurotoxins have been characterized, these being respectively *botulinum* neurotoxin serotypes A, B, $C_1$, D, E, F and G, each of which is distinguished by neutralization with type-specific antibodies. The different serotypes of *botulinum* toxin vary in the animal species that they affect and in the severity and duration of the paralysis they evoke. For example, it has been determined that *botulinum* toxin type A is 500 times more potent, as measured by the rate of paralysis produced in the rat, than is *botulinum* toxin type B. Additionally, *botulinum* toxin type B has been determined to be non-toxic in primates at a dose of 480 U/kg which is about 12 times the primate $LD_{50}$ for *botulinum* toxin type A. Moyer E et al., *Botulinum Toxin Type B: Experimental and Clinical Experience,* being chapter 6, pages 71–85 of "Therapy With *Botulinum* Toxin", edited by Jankovic, J. et al. (1994), Marcel Dekker, Inc. *Botulinum* toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of a motor neuron through a specific interaction between the heavy (or H) chain of the *botulinum* toxin and a neuronal cell surface receptor. The receptor is believed to be different for each type of *botulinum* toxin and for tetanus toxin. The carboxyl end segment of the H chain, $H_C$, appears to be important for targeting of the toxin to the surface of the motor neuron.

In the second step, the toxin crosses the plasma membrane of the motor neuron. The toxin is first engulfed by the cell through receptor-mediated endocytosis, and an endosome containing the toxin is formed. The toxin then escapes the endosome into the cytoplasm of the cell. This step may be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of *botulinum* toxin activity appears to involve reduction of the disulfide bond joining the heavy chain, H chain, and the light (or L) chain of the toxin. The entire toxic activity of *botulinum* toxin and of the tetanus toxin is contained in the L chain of the holotoxin. The L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, *botulinum* toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. *Botulinum* toxin serotype A and E cleave SNAP-25. *Botulinum* toxin serotype C cleaves syntaxin and SNAP-25. Each of the *botulinum* toxins specifically cleaves a different bond, except *botulinum* toxin type B and tetanus toxin which cleave the same bond.

*Botulinum* toxins have been used in clinical settings for the treatment of neuromuscular disorders characterized by hyperactive skeletal muscles. A *botulinum* toxin type A complex has been approved by the U.S. Food and Drug Administration for the treatment of blepharospasm, strabismus and hemifacial spasm. Non-type A *botulinum* toxin serotypes apparently have a lower potency and/or a shorter duration of activity as compared to *botulinum* toxin type A. Most if not all of the *botulinum* toxins can, upon intramuscular injection, produce significant muscle paralysis within one day of the injection, as measured, for example, by the mouse Digit Abduction Score (DAS). Aoki K. R., *Preclinical Update on BOTOX* (*Botulinum Toxin Type A*)—*Purified Neurotoxin Complex Relative to Other Botulinum Toxin Preparations,* Eur J. Neur 1999, 6 (suppl 4):S3–S10. Maximal clinical effect may not result for several days. The typical duration of symptomatic relief from a single intramuscular injection of *botulinum* toxin type A averages about three months. Apparently, a substrate for a *botulinum* toxin can be found in a variety of different cell types. See e.g. *Biochem ,J* 1;339 (pt 1):159–65:1999, and *Mov Disord,* 10(3):376:1995 (pancreatic islet B cells contains at least SNAP-25 and synaptobrevin).

The molecular weight of the *botulinum* toxin protein molecule, for all seven of the known *botulinum* toxin serotypes, is about 150 kD. Interestingly, the *botulinum* toxins are released by *Clostridial bacterium* as complexes comprising the 150 kD *botulinum* toxin protein molecule along with associated non-toxin proteins. Thus, the *botulinum* toxin type A complex can be produced by Clostridial bacterium as 900 kD, 500 kD and 300 kD forms. *Botulinum* toxin types B and $C_1$ are apparently produced as only a 700 kD or 500 kD complex. *Botulinum* toxin type D is produced as both 300 kD and 500 kD complexes. Finally, *botulinum* toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the *botulinum* toxin molecule comprise the relevant neurotoxin complex) may act to provide stability against denaturation to the *botulinum* toxin molecule and protection against digestive acids when toxin is ingested. Additionally, it is possible that the larger (greater than about 150 kD molecular weight) *botulinum* toxin complexes may result in a slower rate of diffusion of the *botulinum* toxin away from a site of intramuscular injection of a *botulinum* toxin complex.

In vitro studies have indicated that *botulinum* toxin inhibits potassium cation induced release of both acetylcholine and norepinephrine from primary cell cultures of brainstem tissue. Additionally, it has been reported that *botulinum* toxin inhibits the evoked release of both glycine and glutamate in primary cultures of spinal cord neurons and that in brain synaptosome preparations *botulinum* toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain,* J Neurochem 51(2); 522–527:1988) CGRP, substance P and glutamate (Sanchez-Prieto, J., et al., *Botulinum* Toxin A Blocks Glutamate *Exocytosis From Guinea Pig Cerebral Cortical Synaptosomes,* Eur J. Biochem 165;675–681:1897. Thus, when adequate concentrations are used, stimulus-evoked release of most neurotransmitters is blocked by *botulinum* toxin. See e.g. Pearce, L. B., *Pharmacologic Characterization of Botulinum Toxin For Basic Science and Medicine*, Toxicon 35(9); 1373–1412 at 1393; Bigalke H., et al., *Botulinum A Neurotoxin Inhibits Non-Cholinergic Synaptic Transmission in Mouse Spinal Cord Neurons in Culture,* Brain Research 360; 318–324:1985; Habermann E., *Inhibition by Tetanus and Botulinum A Toxin of the release of* [$^3H$]*Noradrenaline and* [$^3H$]*GABA From Rat Brain Homogenate*, Experientia 44; 224–226:1988, Bigalke H., et al., *Tetanus Toxin and Botulinum A Toxin Inhibit Release and Uptake of Various Transmitters, as Studied with Particulate*

*Preparations From Rat Brain and Spinal Cord*, Naunyn-Schmiedeberg's Arch Pharmacol 316;244–251:1981, and; Jankovic J. et al., *Therapy With Botulinum Toxin,* Marcel Dekker, Inc., (1994), page 5.

*Botulinum* toxin type A can be obtained by establishing and growing cultures of *Clostridium botulinum* in a fermenter and then harvesting and purifying the fermented mixture in accordance with known procedures. All the *botulinum* toxin serotypes are initially synthesized as inactive single chain proteins which must be cleaved or nicked by proteases to become neuroactive. The bacterial strains that make *botulinum* toxin serotypes A and G possess endogenous proteases and serotypes A and G can therefore be recovered from bacterial cultures in predominantly their active form. In contrast, *botulinum* toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the *botulinum* toxin type B serotype only cleave a portion of the toxin produced. The exact proportion of nicked to unnicked molecules depends on the length of incubation and the temperature of the culture. Therefore, a certain percentage of any preparation of, for example, the *botulinum* toxin type B toxin is likely to be inactive, possibly accounting for the known significantly lower potency of *botulinum* toxin type B as compared to *botulinum* toxin type A. The presence of inactive *botulinum* toxin molecules in a clinical preparation will contribute to the overall protein load of the preparation, which has been linked to increased antigenicity, without contributing to its clinical efficacy. Additionally, it is known that *botulinum* toxin type B has, upon intramuscular injection, a shorter duration of activity and is also less potent than *botulinum* toxin type A at the same dose level.

High quality crystalline *botulinum* toxin type A can be produced from the Hall A strain of *Clostridium botulinum* with characteristics of $\geqq 3\times10^7$ U/mg, an $A_{260}/A_{278}$ of less than 0.60 and a distinct pattern of banding on gel electrophoresis. The known Shantz process can be used to obtain crystalline *botulinum* toxin type A, as set forth in Shantz, E. J., et al, *Properties and Use of Botulinum Toxin and Other Microbial Neurotoxins in Medicine,* Microbiol Rev. 56; 80–99:1992. Generally, the *botulinum* toxin type A complex can be isolated and purified from an anaerobic fermentation by cultivating *Clostridium botulinum* type A in a suitable medium. The known process can also be used, upon separation out of the non-toxin proteins, to obtain pure *botulinum* toxins, such as for example: purified *botulinum* toxin type A with an approximately 150 kD molecular weight with a specific potency of $1–2\times10^8$ $LD_{50}$ U/mg or greater; purified *botulinum* toxin type B with an approximately 156 kD molecular weight with a specific potency of $1–2\times10^8$ $LD_{50}$ U/mg or greater, and; purified *botulinum* toxin type F with an approximately 155 kD molecular weight with a specific potency of $1–2\times10^7$ $LD_{50}$ U/mg or greater.

*Botulinum* toxins and/or *botulinum* toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo.

Both pure *botulinum* toxin and *botulinum* toxin complexes can be used to prepare a pharmaceutical composition. Both pure *botulinum* toxin and *botulinum* toxin complexes, such a toxin type A complex are susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the *botulinum* toxins (which are intracellular peptidases) is dependant, at least in part, upon their three dimensional conformation. Thus, *botulinum* toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available *botulinum* toxin containing pharmaceutical composition is sold under the trademark BOTOX® (available from Allergan, Inc., of Irvine, Calif.). BOTOX® consists of a purified *botulinum* toxin type A complex, albumin and sodium chloride packaged in sterile, vacuum-dried form. The *botulinum* toxin type A is made from a culture of the Hall strain of *Clostridium botulinum* grown in a medium containing N-Z amine and yeast extract. The *botulinum* toxin type A complex is purified from the culture solution by a series of acid precipitations to a crystalline complex consisting of the active high molecular weight toxin protein and an associated hemaglutinin protein. The crystalline complex is re-dissolved in a solution containing saline and albumin and sterile filtered (0.2 microns) prior to vacuum drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology,* 48:249–53:1997.

It has been reported that *botulinum* toxin type A has been used in clinical settings as follows:

(1) about 75–125 units of BOTOX® per intramuscular injection (multiple muscles) to treat cervical dystonia;

(2) 5–10 units of BOTOX® per intramuscular injection to treat glabellar lines (brow furrows) (5 units injected intramuscularly into the procerus muscle and 10 units injected intramuscularly into each corrugator supercilii muscle);

(3) about 30–80 units of BOTOX® to treat constipation by intrasphincter injection of the puborectalis muscle;

(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
 (a) flexor digitorum profundus: 7.5 U to 30 U
 (b) flexor digitorum sublimus: 7.5 U to 30 U
 (c) flexor carpi ulnaris: 10 U to 40 U
 (d) flexor carpi radialis: 15 U to 60 U
 (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular *botulinum* toxin has been used in the treatment of tremor in patients with Parkinson's disease, although it has been reported that results have not been impressive. Marjama-Jyons, J., et al., *Tremor-Predominant Parkinson's Disease, Drugs & Aging* 16(4); 273–278:2000.

It is known that *botulinum* toxin type A can have an efficacy for up to 12 months (*European J. Neurology* 6 (Supp 4): S111–S1150:1999), and in some circumstances for as long as 27 months. *The Laryngoscope* 109:1344–1346:1999. However, the usual duration of an intramuscular injection of Botox® is typically about 3 to 4 months.

The success of *botulinum* toxin type A to treat a variety of clinical conditions has led to interest in other *botulinum* toxin serotypes. A study of two commercially available *botulinum* type A preparations (BOTOX® and Dysport®) and preparations of *botulinum* toxins type B and F (both obtained from Wako Chemicals, Japan) has been carried out to determine local muscle weakening efficacy, safety and antigenic potential. *Botulinum* toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX® (5.0 to 10.0 units/kg) or *botulinum* toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for *botulinum* toxin type B or 0.15 ng/kg for BOTOX®). Peak muscle weakness and duration were dose related for all serotypes. DAS $ED_{50}$ values (units/kg) were as follows: BOTOX®: 6.7, Dysport®: 24.7,*botulinum* toxin type B: 27.0 to 244.0, *botulinum* toxin type F: 4.3. BOTOX® had a longer duration of action than *botulinum* toxin type B or *botulinum* toxin type F. Therapeutic index values were as follows: BOTOX®: 10.5, Dysport®: 6.3, *botulinum* toxin type B: 3.2. Water consumption was greater in mice injected with *botulinum* toxin type B than with BOTOX®, although *botulinum* toxin type B was less effective at weakening muscles. After four months of injections 2 of 4 (where treated with 1.5 ng/kg) and 4 of 4 (where treated with 6.5 ng/kg) rabbits developed antibodies against *botulinum* toxin type B. In a separate study, 0 of 9 BOTOX® treated rabbits demonstrated antibodies against *botulinum* toxin type A. DAS results indicate relative peak potencies of *botulinum* toxin type A being equal to *botulinum* toxin type F, and *botulinum* toxin type F being greater than *botulinum* toxin type B. With regard to duration of effect, *botulinum* toxin type A was greater than *botulinum* toxin type B, and *botulinum* toxin type B duration of effect was greater than *botulinum* toxin type F. As shown by the therapeutic index values, the two commercial preparations of *botulinum* toxin type A (BOTOX® and Dysport®) are different. The increased water consumption behavior observed following hind limb injection of *botulinum* toxin type B indicates that clinically significant amounts of this serotype entered the murine systemic circulation. The results also indicate that in order to achieve efficacy comparable to *botulinum* toxin type A, it is necessary to increase doses of the other serotypes examined. Increased dosage can comprise safety. Furthermore, in rabbits, type B was more antigenic than was BOTOX®, possibly because of the higher protein load injected to achieve an effective dose of *botulinum* toxin type B. *Eur J Neurol* 1999 Nov;6(Suppl 4):S3–S10.

In addition to having pharmacologic actions at the peripheral location, *botulinum* toxins may also have inhibitory effects in the central nervous system. Work by Weigand et al, *Nauny-Schmiedeberg's Arch. Pharmacol.* 1976; 292, 161–165, and Habermann, *Nauny-Schmiedeberg's Arch. Pharmacol.* 1974; 281, 47–56 showed that *botulinum* toxin is able to ascend to the spinal area by retrograde transport. As such, a *botulinum* toxin injected at a peripheral location, for example intramuscularly, may be retrograde transported to the spinal cord.

Acetylcholine

Typically only a single type of small molecule neurotransmitter is released by each type of neuron in the mammalian nervous system. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. *Botulinum* toxin inhibits the release of both types of compounds from both types of cells in vitro, permeabilized (as by electroporation) or by direct injection of the toxin into the denervated cell. *Botulinum* toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

As indicated above, the drugs presently being used to treat illnesses related to gonadotrophins are often accompanied by detrimental side effects. There continues to be a need for an improved agent and method for treating gonadotrophin related illnesses.

SUMMARY OF THE INVENTION

The following definitions apply herein:

"About" means approximately or nearly and in the context of a numerical value or range set forth herein means ±10% of the numerical value or range recited or claimed.

"Local administration" means direct administration of a pharmaceutic at or to the vicinity of a site on or within an animal body, at which site a biological effect of the pharmaceutic is desired. Local administration excludes systemic routes of administration, such as intravenous or oral administration.

"Intracranial" means within the cranium or at or near the dorsal end of the spinal cord and includes the medulla, brain stem, pons, cerebellum and cerebrum. The neurohumoral pathway and the pituitary are both considered to be intracranial.

"Clostridial toxins" include *botulimum* toxin, butyricum toxin and tetani toxins.

"Light chain component" comprises a light chain and/or a fragment thereof of a Clostridial toxin. The light chain has a molecular weight of about 50 kDa, and may be referred to as L chain or L. A light chain or a fragment thereof may have proteolytic activity.

"Heavy chain component" comprises a heavy chain and/ or a modified heavy chain of a Clostridial toxin. The full-length heavy chain has a molecular weight of about 100 kDa and can be referred to as H chain or as H. A heavy chain comprises an $H_C$ and an $H_N$. A modified heavy chain may be a fragment of a heavy chain, for example, $H_N$.

"$H_C$" means a fragment derived from the H chain of a Clostridial toxin which is approximately equivalent, for example functionally equivalent, to the carboxyl end fragment of the H chain, or the portion corresponding to that fragment in the intact H chain involved in binding to cell surfaces.

"$H_N$" means a fragment derived from the H chain of a Clostridial toxin which is approximately equivalent, for example functionally equivalent, to the amino end segment of the H chain, or the portion corresponding to that fragment in the intact H chain involved in the translocation of at least the L chain across an intracellular endosomal membrane into a cytoplasm of a cell. An $H_N$, may result from an $H_c$ being removed from an H chain. An $H_N$ may also result from an H chain being modified such that its $H_c$ no longer binds to cholinergic cell surfaces.

"$LH_N$" means a fragment derived from a Clostridial toxin that contains the L chain, or a functional fragment thereof coupled to the $H_N$ fragment. $LH_N$ can be obtained from the intact Clostridial toxin by chemical modification or removal of the $H_c$ domain by methods known to those skilled in the art.

"Targeting component" means a chemical moiety which is able to preferentially bind to a cell surface receptor, for example, a GnRH receptor, under physiological conditions.

"GnRH" means gonadotrophin-releasing hormone.

"GnRH-A" means an analog of GnRH.

"Variable region" means the part of an antibody that varies extensively from one antibody to another as a result of alternative subunit sequences. The variable region can specifically bind to an antigen, for example, a GnRH receptor.

"Spacer" means a molecule or set of molecules which physically separate and add distance between the components. One function of a spacer is to prevent steric hindrance between the components. For example, an agent of the present invention may be: L-linker-spacer-linker-$H_N$-linker-GnRH.

"Linker" means a molecule which couples two or more other molecules or components together.

"Variant" means a molecule or peptide which is substantially the same as that of the referenced molecule or peptide in its identity and function. For example, a variant of a referenced light chain has slight and non-consequential sequence variations from the referenced light chain. In one embodiment, variants are considered to be equivalent to the disclosed sequences and as such are within the scope of the invention.

In accordance with the present invention, an agent is featured comprising (1) a light chain component which comprises a light chain or a fragment thereof of a *botulimum* toxin, a butyricum toxin, a tetani toxin or variants thereof, (2) a translocation component which comprises a heavy chain or a modified heavy chain of a *botulimum* toxin, a butyricum toxin, a tetani toxin or variants thereof; and (3) a targeting component which selectively binds to a GnRH receptor.

Further in accordance with the present invention, the agent may be useful for decreasing gonadotrophin secretion in a mammal, for example, a human being. In one embodiment the agent of the invention is used to treat the symptom of a pituitary hormone related disease, particularly gonadotrophin related illnesses, for example, breast cancer, prostate cancer, pancreatic cancer, endometriosis, endometrial cancer or precocious puberty.

Still further in accordance with the present invention, the light chain component is a light chain or a fragment of a *botulinum* toxin type A, B, $C_1$, D, E, F, G or variants thereof. The light chain component decreases the release of hormones from a cell. Preferably, the effect(s) of the light chain component is/are reversible.

Still further in accordance with the present invention, the translocation component comprises a heavy chain or a modified heavy chain of a *botulinum* toxin type A, B, $C_1$, D, E, F, G or variants thereof. The translocation component facilitates the transfer of the light chain component into the cytoplasm of a cell.

Still further in accordance with the present invention, the targeting component is an amino acid component that can selectively bind to a GnRH receptor under physiological conditions. In one embodiment, the amino acid component is the variable region of an antibody. In a preferred embodiment, the amino acid component is a peptide. In one embodiment, the peptide may be a GnRH or an analog thereof (hereinafter "GnRH-A") represented by the amino acid sequence:

pyroGlu-His-Trp-Ser-Try-X-Leu-Arg-Pro-Z (SEQ ID NO: 46)

wherein X is an amino acid selected from the group consisting of glycine, lysine, D-lysine, ornithine, D-ornithine glutamic acid, D-glutamic acid, aspartic acid, D-aspartic acid, cysteine, D-cysteine, tyrosine and D-tyrosine; and Z is a substituent selected from the group consisting of Gly-$NH_2$, ethylamide, and Aza-Gly-$NH_2$.

Still further, in accordance with the present invention, the agent may comprise only a portion of the GnRH or GnRH-A. For example, an agent of the present invention may comprise a polypeptide having 8 consecutive amino acids, 7 consecutive amino acids, 6 consecutive amino acids or 5 consecutive amino acids of GnRH or GnRH-A.

Still further in accordance with the present invention, the agent is linked to a facilitator component. The facilitator component is able to facilitate the transfer of the agent across a blood brain barrier.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DETAILED DESCRIPTION OF THE INVENTION

Figure 1A:
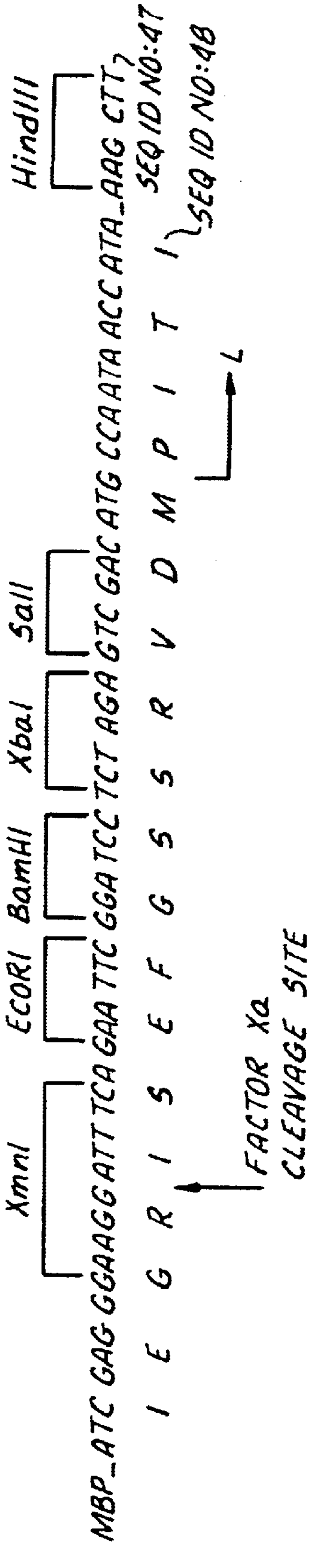
FIG. 1 is a schematic representation of the tetani toxin (hereinafter "TeTx") and the DNA construct (pMAL-L) used to express the fusion proteins comprising a light chain and a maltose binding protein, referred to herein as the MBP-L chain fusion proteins. The single-letter code in the first part of the figure represents the amino acid sequence of the first several residues of the purified recombinant L chain determined by N-terminal microsequencing. The second part of the figure shows the H chain is disulfide bonded to the L chain. The location of the zinc-binding domain is also diagrammed.
Figure 1B:
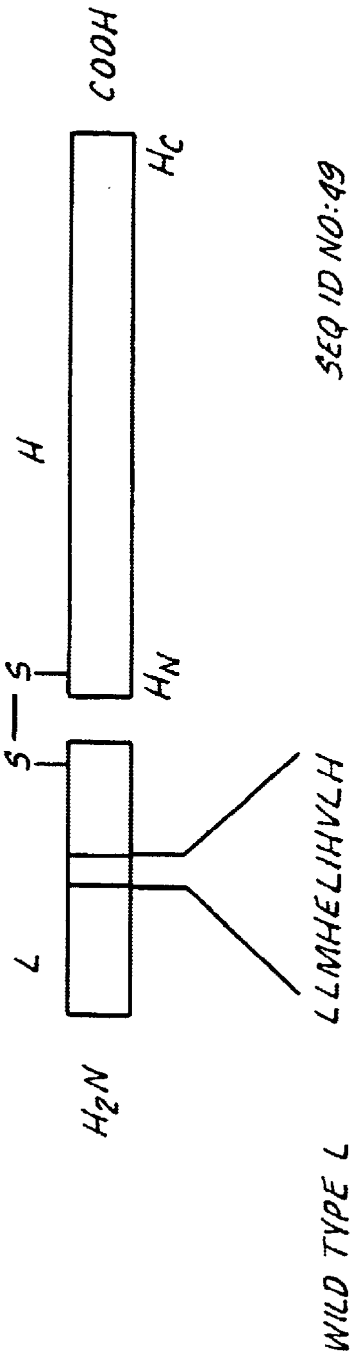

The present invention relates to agents and methods for treating sex hormone related diseases, for example gonadotrophin related illnesses. Without wishing to limit the invention to any theory or mechanism of operation, it is believed that the agents of the present invention are effectively used to lower the level of gonadotrophin secretion in a mammal and thereby treat or alleviate illnesses associated with an elevated level of gonadotrophin.

In a broad embodiment, an agent of this invention comprises a light chain component, a translocation component, and a targeting component.

The light chain component may include a light chain of a *botulinum* toxin, a butyricum toxin, a tetani toxin or biologically active variants of these toxins. The light chain component may also include a fragment of the mentioned light chains, providing that the fragments are biologically active in a physiological environment. That is, these fragments can substantially interfere with the release of hormones from a cell. In a preferred embodiment, the light chain component includes a light chain of a *botulinum* toxin type A, B, $C_1$, D, E, F, G or biologically active variants of these serotypes. In another preferred embodiment, the light chain component may even be fragments of the *botulinum* toxin type A, B, $C_1$, D, E, E, F, G or the biologically active variants of these serotypes, provided that the fragments themselves are biologically active, for example the fragment is able to interfere with the release of hormones from a cell. In one preferable embodiment, the light chain component of this invention is not cytotoxic, that is their effect(s) is/are reversible.

In one embodiment, the light chain component can exert its effect from inside a cell, for example, from inside a pituitary gonadotroph. In one embodiment, an agent with a light chain exerting its effect from inside a cell further comprises a translocation component. The translocation component is able to facilitate the transfer of at least a part of the agent into the cytoplasm of the target cell.

In a broad embodiment, the translocation component comprises a heavy chain. In one embodiment, the translocation component comprises a modified heavy chain. The modified heavy chain may comprise an $H_N$ component. For example, a modified heavy chain may include an amino terminal of a *botulinum* toxin, a butyricum toxin, a tetani toxin or variants thereof. Preferably, the modified heavy chain includes an amino terminal of a *botulinum* toxin type A, B, $C_1$, D, E, F, G or variants thereof. More preferably, the modified heavy chain comprises an amino terminal of a *botulinum* toxin type A. Even more preferably, the modified heavy chain comprises an amino terminal fragment of a heavy chain of *botulinum* toxin type A, which is capable of facilitating the translocation of at least part of the agent, for example the therapeutic component, from inside a vesicle into the cytoplasm of a cell.

In a preferred embodiment, an agent according to this invention comprises a light chain component comprising a light chain of a *botulinum* toxin type A and the translocation component comprising an $H_N$ of a *botulinum* toxin type A, wherein the $H_N$ can assist in the translocation of at least the therapeutic component into a cytoplasm of a cell.

In another embodiment, an agent according to this invention comprises a therapeutic component comprising a light chain of one type of *botulinum* toxin and a translocation component comprising an $H_N$, or a fragment of an $H_N$, of another *botulinum* toxin, constituting a chimeric protein. For example, in one preferred embodiment, an agent in accordance with the invention comprises $LH_N$ whereof the L chain is derived from *botulinum* toxin type B and the $H_N$ is derived from *botulinum* toxin type A. In this example, an $H_N$ fragment of the *botulinum* toxin type A is produced according to the method described by Shone et al. (1987, *Eur. J. Biochem.* 167, 175–180). The L chain of *botulinum* toxin type B is produced according to the method of Sathyamoorthy and DasGupta (1985, *J. Biol. Chem.* 260, 10461–10466). The free cysteine on the amine end segment of the H chain fragment of *botulinum* toxin type A is then derivatized by the addition of a ten-fold molar excess of dipyridyl disulphide followed by incubation at 4 degree C. overnight. The excess dipyridyl disulphide and the thiopyridone by product are then removed by desalting the protein over a PDIO column (Pharmacia) into PBS. The derivatized $H_N$ is then concentrated to a protein concentration in excess of 1 mg/ml before being mixed with an equimolar portion of L chain from *botulinum* toxin type B (>1 mg/ml in PBS). After overnight incubation at room temperature the mixture is separated by size exclusion chromatography over Superose 6 (Pharmacia), and the fractions analyzed by SDS-PAGE. The chimeric $LH_N$ is then available for dramatization to produce a targeted conjugate.

In one embodiment, the light chain component and the translocation component are originally derived from a *botulinum* toxin, preferably *botulinum* toxin type A. For example, an $LH_N$ may be produced by recombinant techniques or chemically modifying the heavy chain of a di-chain *botulinum* toxin to eliminate the $H_C$ portion: it is well known in the art that the $H_C$ of the neurotoxin molecule, for example *botulinum* toxin type A, can be removed from the other segment of the H chain, the $H_N$, such that the $H_N$ fragment remains disulphide linked to the L chain of the neurotoxin molecule to provide a $LH_N$ fragment. This fragment may be covalently coupled to a targeting component forming an agent of the present invention.

In a broad embodiment, a targeting component of this invention is able to bind to a specific target cell receptor, for example, a GnRH receptor, preferably the pituitary GnRH receptor.

In a broad embodiment, the targeting component comprises an amino acid component. In one embodiment, the amino acid component comprises an antibody which will specifically bind a GnRH receptor, preferably a pituitary GnRH receptor. In a preferred embodiment, the targeting component comprises an Fab portion of an antibody which binds to a GnRH receptor. In an even more preferred embodiment, the targeting component comprises a variable region of an antibody. The variable region may be produced recombinantly in accordance with techniques which are well known in the art.

In one embodiment, the amino acid component comprises a peptide. The peptide may include, for example, a GnRH. GnRH is a decapeptide and has the following chemical structure:

pyro Glu-His-Trp-Ser-Tyr-Gly-Leu-Arg-Pro-Gly (SEQ ID 1)

In one embodiment, the peptide may also include analogs of GnRH (GnRH-A). In a preferred embodiment, the general structure of a GnRH-A is:

pyroGlu-His-Trp-Ser-Tyr-X-Leu-Arg-Pro-Z (SEQ ID NO: 46)

wherein X is any amino acid, but preferably the amino acids glycine, lysine, D-lysine, ornithine, D-ornithine glutamic acid, D-glutamic acid, aspartic acid, D-aspartic acid, cysteine, D-cysteine, tyrosine or D-tyrosine; and Z is a substituent selected from the group consisting of Gly-$NH_2$, ethylamide, and Aza-Gly-$NH_2$.

Within the possibilities of this general structure, a particularly preferred GnRH-A is:

PyroGlu-His-Trp-Ser-Tyr-D-Lys-Leu-Arg-Pro-ethylamide (SEQ ID NO: 9)

Table 1 identifies the various, non-limiting, examples of the GnRH-A.

TABLE 1

| | |
|---|---|
| SEQ ID 1 | PyroGlu-His-Trp-Ser-Tyr-Gly-Leu-Arg-Pro-Gly |
| SEQ ID 2 | PyroGlu-His-Trp-Ser-Tyr-Gly-Leu-Arg-Pro-Gly-$NH_2$ |
| SEQ ID 3 | PyroGlu-His-Trp-Ser-Tyr-Gly-Leu-Arg-Pro-ethylamide |
| SEQ ID 4 | PyroGlu-His-Trp-Ser-Tyr-Gly-Leu-Arg-Pro-Aza-Gly-$NH_2$ |
| SEQ ID 5 | PyroGlu-His-Trp-Ser-Tyr-Lys-Leu-Arg-Pro-Gly-$NH_2$ |
| SEQ ID 6 | PyroGlu-His-Trp-Ser-Tyr-Lys-Leu-Arg-Pro-ethylamide |
| SEQ ID 7 | PyroGlu-His-Trp-Ser-Tyr-Lys-Leu-Arg-Pro-Aza-Gly-$NH_2$ |
| SEQ ID 8 | PyroGlu-His-Trp-Ser-Tyr-D-Lys-Leu-Arg-Pro-Gly-$NH_2$ |
| SEQ ID 9 | PyroGlu-His-Trp-Ser-Tyr-D-Lys-Leu-Arg-Pro-ethylamide |
| SEQ ID 10 | PyroGlu-His-Trp-Ser-Tyr-D-Lys-Leu-Arg-Pro-Aza-Gly-$NH_2$ |
| SEQ ID 11 | PyroGlu-His-Trp-Ser-Tyr-Ornithine-Leu-Arg-Pro-Gly-$NH_2$ |
| SEQ ID 12 | PyroGlu-His-Trp-Ser-Tyr-Ornithine-Leu-Arg-Pro-ethylamide |
| SEQ ID 13 | PyroGlu-His-Trp-Ser-Tyr-Ornithine-Leu-Arg-Pro-Aza-Gly-$NH_2$ |
| SEQ ID 14 | PyroGlu-His-Trp-Ser-Tyr-D-Ornithine-Leu-Arg-Pro-Gly-$NH_2$ |

TABLE 1-continued

| | |
|---|---|
| SEQ ID 15 | PyroGlu-His-Trp-Ser-Tyr-D-Ornithine-Leu-Arg-Pro-ethylamide |
| SEQ ID 16 | PyroGlu-His-Trp-Ser-Tyr-D-Ornithine-Leu-Arg-Pro-Aza-Gly-$NH_2$ |
| SEQ ID 17 | PyroGlu-His-Trp-Ser-Tyr-Glu-Leu-Arg-Pro-Gly-$NH_2$ |
| SEQ ID 18 | PyroGlu-His-Trp-Ser-Tyr-Glu-Leu-Arg-Pro-ethylamide |
| SEQ ID 19 | PyroGlu-His-Trp-Ser-Tyr-Glu-Leu-Arg-Pro-Aza-Gly-$NH_2$ |
| SEQ ID 20 | PyroGlu-His-Trp-Ser-Tyr-D-Glu-Leu-Arg-Pro-Gly-$NH_2$ |
| SEQ ID 21 | PyroGlu-His-Trp-Ser-Tyr-D-Glu-Leu-Arg-Pro-ethylamide |
| SEQ ID 22 | PyroGlu-His-Trp-Ser-Tyr-D-Glu-Leu-Arg-Pro-Aza-Gly-$NH_2$ |
| SEQ ID 23 | PyroGlu-His-Trp-Ser-Tyr-Asp-Leu-Arg-Pro-Gly-$NH_2$ |
| SEQ ID 24 | PyroGlu-His-Trp-Ser-Tyr-Asp-Leu-Arg-Pro-ethylamide |
| SEQ ID 25 | PyroGlu-His-Trp-Ser-Tyr-Asp-Leu-Arg-Pro-Aza-Gly-$NH_2$ |
| SEQ ID 26 | PyroGlu-His-Trp-Ser-Tyr-D-Asp-Leu-Arg-Pro-Gly-$NH_2$ |
| SEQ ID 27 | PyroGlu-His-Trp-Ser-Tyr-D-Asp-Leu-Arg-Pro-ethylamide |
| SEQ ID 28 | PyroGlu-His-Trp-Ser-Tyr-D-Asp-Leu-Arg-Pro-Aza-Gly-$NH_2$ |
| SEQ ID 29 | PyroGlu-His-Trp-Ser-Tyr-Cys-Leu-Arg-Pro-Gly-$NH_2$ |
| SEQ ID 30 | PyroGlu-His-Trp-Ser-Tyr-Cys-Leu-Arg-Pro-ethylamide |
| SEQ ID 31 | PyroGlu-His-Trp-Ser-Tyr-Cys-Leu-Arg-Pro-Aza-Gly-$NH_2$ |
| SEQ ID 32 | PyroGlu-His-Trp-Ser-Tyr-D-Cys-Leu-Arg-Pro-Gly-$NH_2$ |
| SEQ ID 33 | PyroGlu-His-Trp-Ser-Tyr-D-Cys-Leu-Arg-Pro-ethylamide |
| SEQ ID 34 | PyroGlu-His-Trp-Ser-Tyr-D-Cys-Leu-Arg-Pro-Aza-Gly-$NH_2$ |
| SEQ ID 35 | PyroGlu-His-Trp-Ser-Tyr-Tyr-Leu-Arg-Pro-Gly-$NH_2$ |
| SEQ ID 36 | PyroGlu-His-Trp-Ser-Tyr-Tyr-Leu-Arg-Pro-ethylamide |
| SEQ ID 37 | PyroGlu-His-Trp-Ser-Tyr-Tyr-Leu-Arg-Pro-Aza-Gly-$NH_2$ |
| SEQ ID 38 | PyroGlu-His-Trp-Ser-Tyr-D-Tyr-Leu-Arg-Pro-Gly-$NH_2$ |
| SEQ ID 39 | PyroGlu-His-Trp-Ser-Tyr-D-Tyr-Leu-Arg-Pro-ethylamide |
| SEQ ID 40 | PyroGlu-His-Trp-Ser-Tyr-D-Tyr-Leu-Arg-Pro-Aza-Gly-$NH_2$ |

In one embodiment, a targeting component may be linked to a *botulinum* toxin, preferably a *botulinum* toxin without the $H_C$ (such as $LH_N$), to form an agent of the present invention.

In a preferred embodiment, the targeting component is a GnRH-A. For example, a GnRH-A may be linked to a *botulinum* toxin or an $LH_N$ to form an agent of the present invention. Preferably the GnRH-A molecule is linked to an $LH_N$ in a manner as to not substantially interfere with the therapeutic function of L and the translocation function of $H_N$. In one embodiment, an $LH_N$ is linked to position 6 of GnRH-A to form an agent of the present invention. Without wishing to limit the invention to any particular theory or mechanism of operation, it is believed that a linkage to position 6 of the GnRH-A allows for the GnRH-A to effectively bind to a GnRH receptor, preferably a pituitary GnRH receptor.

In a broad embodiment, spacers may be used to physically further separate components of the present invention. For example, an agent of the present invention may comprise an $LH_N$ connected to a GnRH through a spacer. Preferably, a spacer functions to create a distance between the components to minimize or eliminate steric hindrances to the components. Even more preferably, the minimization or elimination of steric hindrances allows the respective components to function more effectively.

In one embodiment, a spacer comprises a proline, serine, threonine and/or cysteine-rich amino acid sequence similar or identical to a human immunoglobulin hinge region. In a preferred embodiment, the spacer comprises the amino acid sequence of an immunoglobulin g1 hinge region. Such a sequence has the sequence:

Glu-Pro-Lys-Ser-Cys-Asp-Lys-Thr-His-Thr-Cys-Pro-Pro-Cys-Pro (SEQ ID 41).

Spacers may also comprise hydrocarbon moieties. For example, such hydrocarbon moieties are represented by the chemical formulas:

$HOOC—(CH_2)_n—COOH$, where n=1–12 or, $HO—(CH_2)_n—COOH$, where n>10

In a broad embodiment, linkers (hereinafter "Linker Y" or "Y") may be used to link together two or more molecules, components and/or spacers. For example, a Linker Y may be used to link a GnRH-A to a $LH_N$. In another embodiment, a Linker Y may be employed to link an $LH_N$ to a spacer; in turn, that spacer may then be linked to GnRH by another Linker Y, forming an agent comprising the structure:

$LH_N$-Y-spacer-Y-GnRH.

Linker Y may be selected from the group consisting of 2-iminothiolane, N-succinimidyl-3-(2-pyridyldithio) propionate (SPDP), 4-succinimidyloxycarbonyl-alpha-(2-pyridyldithio)toluene (SMPT), m-maleimidobenzoyl-N-hydroxysuccinimide ester (MBS), N-succinimidyl (4-iodoacetyl)aminobenzoate (SIAB), succinimidyl 4-(p-maleimidophenyl)butyrate (SMPB), 1-ethyl-3-(3-dimethylaminopropyl)carbodiimide (EDC), bis-diazobenzidine and glutaraldehyde.

In one embodiment, Linker Y may be attached to an amino group, a carboxylic group, a sulfhydryl group or a hydroxyl group of an amino acid group of a component. For example, a Linker Y may be linked to a carboxyl acid group of amino acid of GnRH-A, preferably the amino acid at the 6 position.

Although the described chemistry may be used to couple the components of the described invention, any other coupling chemistry known to those skilled in the art capable of chemically attaching a targeting component to another component of an agent of the invention is covered by the scope of this invention.

In a broad embodiment, an agent of the present invention may further be conjugated to a facilitator component. A facilitator component is at least effective to assist the transportation of the agent across the blood brain barrier.

In one embodiment, a facilitator component includes a cationic lipid molecule. A cationic lipid molecule may be attached to an agent of the present invention, for example $LH_N$-GnRH molecule, through a covalent bond using methods known to those familiar with the art, including the use of Linker Y. Examples of these cationic lipids are disclosed in U.S. Pat. No. 5,459,127, which is incorporated in its entirety herein by reference.

In one embodiment, a facilitator component includes molecules which can undergo receptor mediated transcytosis at the blood brain barrier. Examples of these molecules include, without limitation, insulin, IGF-II and transferrin, Shoichet and Winn (2000, *Advanced Drug Delivery Reviews* 42, 81–102), Laszlo et al. (2000, *Targeting Drugs to the Brain by Redox Chemical Delivery Systems* 377–416).

In a preferred embodiment, the facilitator component is a carrier peptide which can facilitate the transport of an agent of the invention across the blood brain barrier. Such carrier peptides include, for example, a penetratin peptide represented by the formula:

(SEQ ID 42)

Arg-Gly-Gly-Arg-Lys-Ser-Trp-Ser-Arg-

Arg-Arg-Phe-Ser-Thr-Ser-Thr-Gly-Arg

Agents of the present invention have potential utility in human medicine. For example, prostate cancer remains an important cause of cancer deaths and represents the second leading cancer in males. A present method of treating prostate cancer is to castrate the patient to reduce his level of circulating testosterone/DHT, which are thought to propagate the cancer. However, such surgical intervention may be too drastic. Agents of the present invention may be administered, instead, to treat the prostate cancer. For example, an effective dose of $LH_N$-GnRH-insulin may be systemically administered to the patient to reduce serum testosterone/DHT levels to adequately treat the illness.

Agents of the present invention may also be administered to treat endometriosis. Endometriosis is a condition wherein the uterus produces painful growth of endometrial tissue in the female peritoneum and pelvis. This condition may also be treated by reducing the level of circulating gonadotrophin in the patient. As such, an effective dose of the present agent may be administered to reduce the level of gonadotrophin to treat endometriosis.

Those skilled in this art will also appreciate that an agent of this invention may also be administered to treat medical conditions which will benefit from a decrease of gonadotrophin levels in the body. Additional, non-limiting, examples are further provided herein below.

The dose of the agent to be administered depends on many factors. For example, the better each one of the components is able to perform its respective function, the lower the dose of the agent is required to obtain a desired therapeutic effect. One of ordinary skill will be able to readily determine the specific dose for each specific agent. For agents employing a natural, mutated or recombinant *botulinum* toxin A comprising the therapeutic, translocation and targeting component, an effective dose of an agent to be administered may be about 1 U to about 500 U of the *botulinum* toxin.

Furthermore, the amount of the agents administered can vary widely according to the particular disorder being treated, its severity and other various patient variables including size, weight, age, and responsiveness to therapy. Such determinations are routine to one of ordinary skill in the art (see for example, Harrison's Principles of Internal Medicine (1998), edited by Anthony Fauci et al., 14th edition, published by McGraw Hill). In one embodiment, the amount of agent administered is able to lower the secretion of gonadotrophin from the pituitary by about 5% to about 80%, preferably about 30% to about 50%. In another embodiment, the amount of agent administered is able to lower the circulating gonadotrophin level by about 5% to about 80%, preferably about 30% to about 50%.

The routes of administration of the present invention include, but are not limited to, direct injection into the central nervous system. Such injection includes direct intraspinal injection and intracranial injection. It is preferred that the treating physician intracranially apply the agent, for example, $LH_N$-GnRH-A, directly to the pituitary, preferably anterior pituitary. Intracranial injection methods are widely known in the art. For example, U.S. patent application Ser. No. 09/692,811, filed Nov. 20, 2000 discloses various intracranial methods of administering a drug, which may be readily adopted to intracranially administer an agent of the present invention. (See also PCT/US99/17880 (WO 00/07652, which discloses a device useful for chronic intracranial delivery of a drug).

Other routes of administration include, without limitation, transdermal, peritoneal, subcutaneous, intramuscular, intravenous and intrarectal. If it is determined that an agent of the present invention by itself may be unable to pass through the blood brain barrier to reach its target site, preferably the anterior pituitary, it is preferred that a these agents be conjugated to a facilitator component prior to administration.

According to a broad aspect of this invention recombinant techniques are used to produce at least one of the components of the agents. See, for example International Patent Application Publication WO 95/32738, the disclosure of which is incorporated in its entirety herein by reference. The technique includes steps of obtaining genetic materials from DNA cloned from natural sources, or synthetic oligonucleotide sequences, which have codes for one of the components, for example the therapeutic, translocation and/or targeting component (s). The genetic constructs are incorporated into host cells for amplification by first fusing the genetic constructs with a cloning vector, such as a phage, plasmid, phagemid or other gene expression vector. The recombinant cloning vectors are transformed into a mammalian, yeast or bacterial host. The preferred host is *E. coli*. Following expression of recombinant genes in host cells, resultant proteins can be isolated using conventional techniques. The protein expressed may comprise all three components of the agent. For example, the protein expressed may include a light chain of *botulinum* toxin type A (the therapeutic component), an $H_N$ of a *botulinum* toxin type A (the translocation component), and a GnRH-A, which binds a GnRH receptor, preferably an anterior pituitary GnRH receptor, under physiological conditions (a targeting component). In one embodiment, the protein expressed may include less than all three components of the agent. In such case, the components may be chemically joined, preferably through linker Y.

There are many advantages to producing these agents recombinantly. For example, production of toxin from anaerobic *Clostridium* cultures is a cumbersome and time consuming process including a multi-step purification protocol involving several protein precipitation steps and either prolonged and repeated crystallization of the toxin or several stages of column chromatography. Significantly, the high toxicity of the product dictates that the procedure must be performed under strict containment (BL3). During the fermentation process, the folded single chain neurotoxins are activated by endogenous Clostridial proteases through a process termed nicking. This involves the removal of approximately 10 amino acid residues from the single-chain to create the dichain form in which the two chains remain covalently linked through the intra-chain disulfide bond.

The nicked toxin is more active than the unnicked form. The amount and precise location of nicking varies with the serotypes of the bacteria producing the toxin or with the modification made in the outer loop. The differences in single-chain toxin activation and, hence, the yield of nicked toxin, are due to variations in the type and amounts of proteolytic activity produced by a given strain. For example, greater than 99% of *Clostridium botulinum* type A single-chain toxin is activated by the Hall A *Clostridium botulinum* strain, whereas type B and E strains produce toxins with lower amounts of activation (0% to 75% depending upon the fermentation time). Thus, the high toxicity of the mature toxin plays a major part in the commercial manufacture of toxins as therapeutic agents.

The degree of activation of engineered *Clostridial* toxins is, therefore, an important consideration for manufacture of these materials. It would be a major advantage if toxins such as *botulinum* toxin and tetanus toxin could be expressed, recombinantly, in high yield in rapidly-growing bacteria (such as *E. coli* cells) as relatively non-toxic single-chains (or single chains having reduced toxic activity) which are safe, easy to isolate and simple to convert to the fully-active form.

With safety being a prime concern, previous work has concentrated on the expression in *E. coli* and purification of individual H and L chains of tetanus and *botulinum* toxins; these isolated chains are, by themselves, nontoxic; see Li et al. (1994, *Biochemistry* 33, 7014–7020) and Zhou et al. (1995, *Biochemistry* 34, 15175–15181), hereby incorporated by reference herein. Following the separate production of these peptide chains and under strictly controlled conditions the H and L subunits can be combined by oxidative disulphide linkage to form the neuroparalytic di-chains.

In one embodiment, an agent comprising a therapeutic component and a translocation component is recombinantly produced as an unnicked single chain. See Dolly et al. U.S. Ser. No. 09/648,692, the disclosure of which is incorporated in its entirety by reference herein. In a preferred embodiment, the agent includes an amino acid sequence that is susceptible to specific cleavage in vitro following expression as a single chain. Such proteins may include Clostridial toxins and derivatives thereof, such as those proteins disclosed in U.S. Pat. No. 5,989,545 and International Patent Application W095/32738, both incorporated in their entirety by reference herein.

To minimize the safety risk associated with handling neurotoxin, the agents, or toxins of the invention the agent precursors are expressed as their low activity (or inactive) single-chain pro-forms, then, by a carefully controlled proteolytic reaction in vitro, they are activated, preferably to the same potency level as the native neurotoxin from which they were derived. To improve the efficiency and rate of proteolytic cleavage the engineered proteolytic cleavage sites can be designed to occur in a specially designed loop between the H and L portions of the single amino acid chain that promotes accessibility of the protease to the holotoxin substrate.

To reduce the risk of unintentional activation of the toxin by human or commonly encountered proteases, the amino acid sequences of the cleavage site are preferably designed to have a high degree of specificity to proteolytic enzymes which do not normally occur in humans (as either human proteases or occurring in part of the foreseeable human fauna and flora). A non-exclusive list of examples of such proteases includes bovine enterokinase, which cleaves the amino acid sequence DDDDK (SEQ ID NO: 50); tobacco etch virus (TEV) protease, which cleaves the sequence EXXYXQS/G (SEQ ID NO: 51); GENENASE® from *Bacillus amyliquifaciens*, which cleaves the sequence HY or YH; and PRESCISSION® protease from human rhinovirus 3C, which cleaves the amino acid sequence LEVLFQGP (SEQ ID NO: 52). As used above, the letter X indicates any amino acid. All amino acid sequences shown in the present specification are in the direction from amino terminus to carboxyl terminus, and all nucleotide sequences from 5'to 3', (from left to right) unless otherwise indicated.

In one embodiment, the interchain loop region of the *C. botulinum* subtype E toxin, which is normally resistant to proteolytic nicking in the bacterium and mammals, is modified to include the inserted proteolytic cleavage site, and this loop region used as the interchain loop region in the single-chain toxin or modified toxin molecules of the present invention. It is believed that using the loop from *C. botulinum* subtype E will stabilize the unnicked toxin molecule in vivo, making it resistant to undesired cleavage until activated through the use of the selected protease.

In one embodiment, a DNA sequence encoding the $H_C$ is included in the recombinant DNA sequence which encodes the Clostridial toxin contained in the heterologous gene expression system. Therefore, the corresponding $H_C$ portion of an H chain will not be produced. This too will lower the safety risk associated with Clostridial toxin production.

In one embodiment, GnRH may be produced by similar heterologous recombinant DNA expression systems as is familiar to one skilled in the art. In another embodiment, a GnRH or GnRH-A may be produced by standard t-Boc/Fmoc technologies in solution or solid phase as is known to those skilled in the art. Similar synthesis techniques are also covered by the scope of this invention, for example, methodologies employed in Milton et al. (1992, *Biochemistry* 31, 8799–8809) and Swain et al. (1993, *Peptide Research* 6, 147–154).

The following non-limiting examples provide those of ordinary skill in the art with specific preferred methods for treating medical conditions related to gonadotrophin secretions and methods for producing an agent of the present invention. These methods are examples within the scope of the present invention and are not intended to limit the scope of the invention.

EXAMPLE 1

Treatment of Endometriosis

A 34-year-old woman seeks medical attention after undergoing a spontaneous abortion. The patient reports that she has been suffering from dyspareunia (painful intercourse), dysmenorrhea (painful menstruation), and dyschezia (painful bowel evacuation) as early as two years prior to her pregnancy. Physical examination reveals the presence of endometrial tissue outside the lining of the uterine cavity and multiple tender nodules on her uterosacral ligaments. A preliminary diagnosis of endometriosis is confirmed during a laparoscopy-an examination of the peritoneum. The endometriosis is diagnosed as stage III endometriosis indicating a severe case of the disease with stage I being a mild case and stage IV an extensive case.

Surgery is ruled out by the patient because she is of child bearing age and wishes to have children in the future. She is treated with Danazol™, a GnRH agonist. After 4 days of Danazol™ treatment the patient complains of muscular weakness to the point of incapacitation and severe edema. The patient is taken off the drug and continues to suffer from endometriosis.

Subsequently, the physician administers an effective dose of agents of the present invention, for example $LH_N$-GnRH.

The agent is administered intracranially to the anterior pituitary. A method for intracranial administration is set forth in co-pending patent application Ser. No. 09/692,811, “Method for Treating Endocrine Disorders” filed Oct. 20, 2000, incorporated herein by reference in its entirety.

Several days after the administration, the patient notes substantial improvement to her quality of life. Her dyschezia ceases. Over a 2–3 week period she notes reduced symptoms of dysmenorrhea and dyspareunia. After 2 months, a physical examination reveals an overall decrease in the severity of the endometriosis classified now as stage II. At 12 months the endometriosis is classified as stage I. At 18 months a physical examination reveals no sign of endometriosis and the patient is symptom free.

EXAMPLE 2

Treatment of Prostate Cancer

A 54-year-old male tests positive for PSA (prostate specific antigen). The PSA test was administered during a routine physical examination. The patient suffers no symptoms of prostate cancer. A fine needle aspiration biopsy is performed on the patient confirming an early stage prostatic cancer. The patient is treated by intracranial injection of $LH_N$-GnRH administered directly to the anterior pituitary. The dose of $LH_N$-GnRH is sufficient to reduce the patient's level of circulating gonadotrophin by 80% to 30%, preferably 50%.

The patient is monitored closely for advance of the cancer. Over the next 24 months there is no spread of the cancer. Also, there is no detectable further enlargement of the prostate. The treatment is repeated at 27 months. At 36 months from the initial diagnosis, the patient no longer tests positive for PSA.

EXAMPLE 3

Treatment of Precocious Puberty

A 5-year-old female is diagnosed with precocious puberty. Her physical symptoms are development of breasts and growth of pubic hair. The patient has also begun to menstruate in the past month, vaginal smears have detected abnormally high estrogen levels for the patient's age. Urinary tests also show abnormally high levels of gonadotrophins. X-rays of the child's hands, knees, wrists and hips show the beginning signs of epiphyseal closure. The patient's height is in the normal range for a 5 year old child. However, if the condition is left untreated epiphyseal closure will completely stunt the child's growth.

The patient is injected with $LH_N$-GnRH. The dose of $LH_N$-GnRH is sufficient to reduce the patient's level of circulating gonadotrophin by 80% to 30%, preferably 50%. The injection is intracranial and the drug is administered to the anterior pituitary. Within two weeks breast size reduction occurs in the patient. After passage of three months, the patient has not menstruated nor does she show any signs of having reached puberty. After 1 year the patient grows to approximately 80% the height of a normal child her age.

EXAMPLE 4

Treatment of Endometrial Cancer

A woman, age 55, complains during a physical exam of postmenopausal bleeding. Positive diagnosis for early stage endometrial cancer (uterine cancer) is made based on clinical tests, for example, endometrial biopsy and Schiller's test.

A partial hysterectomy is performed on the patient to remove the cancer. In addition, the patient is injected intracranially with $LH_N$-GnRH. The dose of $LH_N$-GnRH is sufficient to reduce the patient's level of circulating gonadotrophin by 80% to 30%, preferably 50%. After 24 months the cancer does not reoccur. The injection is repeated after 27 months.

EXAMPLE 5

Treatment of Breast Cancer

A 42 year old woman seeks a physical medical exam after discovering a lump in her left breast during a routine self breast examination. The patient has a family history of breast cancer and has never conceived a child. These two factors put the patient in a high-risk group for breast cancer. During the clinical evaluation the presence of breast cancer is confirmed. The medical diagnosis consists of a mammography and a needle biopsy.

The cancer appears restricted within a nodule contained within a duct. This, combined with the patient's resistance to a mastectomy procedure, makes her an excellent candidate for a lumpectomy combined with post-operative drug treatment. The lump is surgically removed and the patient is treated with $LH_N$-GnRH by intracranial injection. The dose of $LH_N$-GNRH is sufficient to reduce the patient's pituitary secretion gonadotrophin by about 80% to about 30%, preferably 50%. The patient is checked monthly for the spread of cancer for the first 6 months after surgery and every two months thereafter. Two years after surgery there is no sign of the cancer.

EXAMPLE 6

Subcloning the BoNT/A-L Chain Gene

This example describes the methods to clone the polynucleotide sequence encoding the BoNT/A-L chain. The DNA sequence encoding the BoNT/A-L chain may be amplified by a PCR protocol that employs synthetic oligonucleotides having the sequences, 5'-AAAGGCCTTTTGTTAATAAACAA-3'(SEQ ID 43) and 5'-GGAATTCTTACTTATTGTATCCTTTA-3'(SEQ ID 44). Use of these primers allows the introduction of Stu I and EcoR I restriction sites into the 5' and 3' ends of the BoNT/A-L chain gene fragment, respectively. These restriction sites may be subsequently used to facilitate unidirectional subcloning of the amplification products. Additionally, these primers introduce a stop codon at the C-terminus of the L chain coding sequence. Chromosomal DNA from *C. botulinum* (strain 63 A) may serve as a template in the amplification reaction.

The PCR amplification is performed in a 0.1 mL volume containing 10 mM Tris-HCl (pH 8.3), 50 mM KCl, 1.5 mM MgCl2, 0.2 mM of each deoxynucleotide triphosphate (dNTP), 50 pmol of each primer, 200 ng of genomic DNA and 2.5 units of Taqpolymerase (Promega). The reaction mixture is subjected to 35 cycles of denaturation (1 minute at 94° C.), annealing (2 minutes at 37° C.) and polymerization (2 minutes at 72° C.). Finally, the reaction is extended for an additional 5 minutes at 72° C.

The PCR amplification product may be digested with Stu I and EcoR I, purified by agarose gel electrophoresis, and ligated into Sma I and EcoR I digested pBluescript II SK* to yield the plasmid, pSAL. Bacterial transformants harboring this plasmid may be isolated by standard procedures. The identity of the cloned L chain polynucleotide is confirmed by double stranded plasmid sequencing using SEQUENASE (United States Biochemicals) according to the manufacturer's instructions. Synthetic oligonucleotide sequencing primers are prepared as necessary to achieve overlapping sequencing runs. The cloned sequence is found to be identical to the sequence disclosed by Binz, et al., in *J. Biol. Chem.* 265, 9153 (1990), and Thompson et al., in *Eur. J. Biochem.* 189, 73 (1990). Site-directed mutants designed to compromise the enzymatic activity of the BoNT/A-L chain may also be created.

EXAMPLE 7

Expression of the *Botulinum* Toxin Type A-L (BoNt/A-L) Chain Fusion Proteins This example describes the methods to verify expression of the wild-type L chains, which may serve as a therapeutic component, in bacteria harboring the pCA-L plasmids. Well isolated bacterial colonies harboring either pCAL are used to inoculate L-broth containing 0.1 mg/ml ampicillin and 2% (w/v) glucose, and grown overnight with shaking at 30° C. The overnight cultures are diluted 1:10 into fresh L-broth containing 0.1 mg/ml of ampicillin and incubated for 2 hours. Fusion protein expression is induced by addition of IPTG to a final concentration of 0.1 mM. After an additional 4 hour incubation at 30° C., bacteria are collected by centrifugation at 6,000×g for 10 minutes.

A small-scale SDS-PAGE analysis confirmed the presence of a 90 kDa protein band in samples derived from IPTG-induced bacteria. This Mr is consistent with the predicted size of a fusion protein having MBP (~40 kDa) and BoNT/A-L chain (~50 kDa) components. Furthermore, when compared with samples isolated from control cultures, the IPTG-induced clones contained substantially larger amounts of the fusion protein.

The presence of the desired fusion proteins in IPTG-induced bacterial extracts is also confirmed by western blotting using the polyclonal anti-L chain probe described by Cenci di Bello et al., in *Eur. J. Biochem.* 219, 161 (1993). Reactive bands on PVDF membranes (Pharmacia; Milton Keynes, UK) are visualized using an anti-rabbit immunoglobulin conjugated to horseradish peroxidase (BioRad; Hemel Hempstead, UK) and the ECL detection system (Amersham, UK). Western blotting results confirmed the presence of the dominant fusion protein together with several faint bands corresponding to proteins of lower Mr than the fully sized fusion protein. This observation suggested that limited degradation of the fusion protein occurred in the bacteria or during the isolation procedure. Neither the use of 1 mM nor 10 mM benzamidine (Sigma; Poole, UK) during the isolation procedure eliminated this proteolytic breakdown.

The yield of intact fusion protein isolated by the above procedure remained fully adequate for all procedures described herein. Based on estimates from stained SDS-PAGE gels, the bacterial clones induced with IPTG yielded 5–10 mg of total MBP-wild-type or mutant L chain fusion protein per liter of culture. Thus, the method of producing BoNT/A-L chain fusion proteins disclosed herein is highly efficient, despite any limited proteolysis that did occur.

The MBP-L chain fusion proteins encoded by the pCAL and pCAL-TyrU7 expression plasmids are purified from bacteria by amylose affinity chromatography. Recombinant wild-type or mutant L chains are then separated from the sugar binding domains of the fusion proteins by sitespecific cleavage with Factor $X_2$. This cleavage procedure yielded free MBP, free L chains and a small amount of uncleaved fusion protein. While the resulting L chains present in such mixtures have been shown to possess the desired activities, we have also employed an additional purification step. Accordingly, the mixture of cleavage products is applied to a second amylose affinity column that bound both the MBP and uncleaved fusion protein. Free L chains are not retained on the affinity column, and are isolated for use in experiments described below.

EXAMPLE 8

Purification of Fusion Proteins and Isolation of Recombinant BoNT/A-L Chains This example describes a method to produce and purify wild-type recombinant BoNT/A light chains from bacterial clones. Pellets from 1 liter cultures of bacteria expressing the wild-type BoNT/A-L chain proteins are resuspended in column buffer [10 mM Tris-HCl (pH 8.0), 200 mM NaCl, 1 mM EGTA and 1 mM DTT] containing 1 mM phenylmethanesulfonyl fluoride (PMSF) and 10 mM benzamidine, and lysed by sonication. The lysates are cleared by centrifugation at 15,000×g for 15 minutes at 4° C. Supernatants are applied to an amylose affinity column [2×10 cm, 30 ml resin] (New England BioLabs; Hitchin, UK). Unbound proteins are washed from the resin with column buffer until the eluate is free of protein as judged by a stable absorbance reading at 280 nm. The bound MBP-L chain fusion protein is subsequently eluted with column buffer containing 10 mM maltose. Fractions containing the fusion protein are pooled and dialyzed against 20 mM Tris-HCl (pH 8.0) supplemented with 150 mM NaCl, 2 mM, CaCl2 and 1 mM DTT for 72 hours at 4° C.

Fusion proteins may be cleaved with Factor $X_2$ (Promega; Southampton, UK) at an enzyme: substrate ratio of 1:100 while dialyzing against a buffer of 20 mM Tris-HCl (pH 8.0) supplemented with 150 mM NaCl, 2 mM, $CaCl_2$ and 1 mM DTT. Dialysis is carried out for 24 hours at 4° C. The mixture of MBP and either wild-type or mutant L chain that resulted from the cleavage step is loaded onto a 10 ml amylose column equilibrated with column buffer. Aliquots of the flow through fractions are prepared for SDS-PAGE analysis to identify samples containing the L chains. Remaining portions of the flow through fractions are stored at −20° C. Total *E. coli* extract or the purified proteins are solublized in SDS sample buffer and subjected to PAGE according to standard procedures. Results of this procedure indicated the recombinant toxin fragment accounted for roughly 90% of the protein content of the sample.

The foregoing results indicate that the approach to creating MBP-L chain fusion proteins described herein could be used to efficiently produce wild-type and mutant recombinant BoNT/A-L chains. Further, the results demonstrate that recombinant L chains could be separated from the maltose binding domains of the fusion proteins and purified thereafter.

A sensitive antibody-based assay is developed to compare the enzymatic activities of recombinant L chain products and their native counterparts. The assay employed an antibody having specificity for the intact C-terminal region of SNAP-25 that corresponded to the BoNT/A cleavage site. Western Blotting of the reaction products of BoNT/A cleavage of SNAP-25 indicated an inability of the antibody to bind SNAP-25 sub-fragments. Thus, the antibody reagent employed in the following Example detected only intact SNAP-25. The loss of antibody binding served as an indicator of SNAP-25 proteolysis mediated by added BoNT/A light chain or recombinant derivatives thereof.

EXAMPLE 9

Evaluation of the Proteolytic Activities of Recombinant L Chains Against a SNAP-25 Substrate Both native and recombinant BoNT/A-L chains can proteolyze a SNAP-25 substrate. A quantitative assay may be employed to compare the abilities of the wild-type and their recombinant analogs to cleave a SNAP-25 substrate. The substrate utilized for this assay is obtained by preparing a glutathione-S-transferase (GST)-SNAP-25 fusion protein, containing a cleavage site for thrombin, expressed using the pGEX-2T vector and purified by affinity chromatography on glutathione agarose. The SNAP-25 is then cleaved from the fusion protein using thrombin in 50 mM Tris-HCl (pH 7.5) containing 150 mM NaCl and 2.5 mM $CaCl_2$ (Smith et al. *Gene* 67, 31 (1988) at an enzyme:substrate ratio of 1:100. Uncleaved fusion protein and the cleaved glutathione-binding domain bound to the gel. The recombinant SNAP-25 protein is eluted with the latter buffer and dialyzed against 100 mM HEPES (pH 7.5) for 24 hours at 4° C. The total protein concentration is determined by routine methods.

Rabbit polyclonal antibodies specific for the C-terminal region of SNAP-25 are raised against a synthetic peptide having the amino acid sequence, CANQRATKMLGSG (SEQ ID 45). This peptide corresponded to residues 195 to 206 of the synaptic plasma membrane protein and an N-terminal cysteine residue not found in native SNAP-25. The synthetic peptide is conjugated to bovine serum albumin (BSA) (Sigma; Poole, UK) using maleimidobenzoyl-N-hydroxysuccinimide ester (MBS) as a cross-linking agent (Sigma; Poole, UK) to improve antigenicity (Liu et al., *Biochemistry* 18, 690 (1979). Affinity purification of the anti-peptide antibodies is carried out using a column having the antigenic peptide conjugated via its N-terminal cysteine residue to an aminoalkyl agarose resin (Bio-Rad; Hemel Hempstead, UK), activated with iodoacetic acid using the cross-linker ethyl 3-(3-dimethytpropyl)carbodiimide. After successive washes of the column with a buffer containing 25 mM Tris-HCl (pH 7.4) and 150 mM NaCl, the peptide-specific antibodies are eluted using a solution of 100 mM glycine (pH 2.5) and 200 mM NaCl, and collected in tubes containing 0.2 ml of 1 M Tris-HCl (pH 8.0) neutralizing buffer.

All recombinant preparations containing wild-type L chain are dialyzed overnight at 4° C. into 100 mM HEPES (pH 7.5) containing 0.02% Lubrol and 10 $\mu$M zinc acetate before assessing their enzymatic activities. BoNT/A, previously reduced with 20 mM DTT for 30 minutes at 37° C., as well as these dialyzed samples, are then diluted to different concentrations in the latter HEPES buffer supplemented with 1 mM DTT.

Reaction mixtures include 5 $\mu$l recombinant SNAP-25 substrate (8.5 $\mu$M final concentration) and either 20 $\mu$l reduced BoNT/A or recombinant wild-type L chain. All samples are incubated at 37° C. for 1 hour before quenching the reactions with 25 $\mu$l aqueous 2% trifluoroacetic acid (TFA) and 5 mM EDTA, Foran et al. (1994, *Biochemistry* 33, 15365). Aliquots of each sample are prepared for SDS-PAGE and Western blotting with the polyclonal SNAP-25 antibody by adding SDS-PAGE sample buffer and boiling. Anti-SNAP-25 antibody reactivity is monitored using an ECL detection system and quantified by densitometric scanning.

Western blotting results indicate clear differences between the proteolytic activities of the purified mutant L chain and either native or recombinant wild-type BoNT/A-L chain. Specifically, recombinant wild-type L chain cleaves the SNAP-25 substrate, though somewhat less efficiently than the reduced BoNT/A native L chain that serves as the positive control in the procedure. Thus, an enzymatically active form of the BoNT/A-L chain is produced by recombinant means and subsequently isolated. Moreover, substitution of a single amino acid in the L chain protein abrogated the ability of the recombinant protein to degrade the synaptic terminal protein.

As a preliminary test of the biological activity of the wild-type recombinant BoNT/A-L chain, the ability of the MBP-L chain fusion protein to diminish $Ca^{2+}$-evoked catecholamine release from digitonin-permeabilized bovine adrenochromaffin cells is examined. Consistently, wild-type recombinant L chain fusion protein, either intact or cleaved with Factor $X_2$ to produce a mixture containing free MBP and recombinant L chain, induced a dose-dependent inhibition of $Ca^{2+}$-stimulated release equivalent to the inhibition caused by native BoNT/A.

EXAMPLE 10

Reconstitution of Native L Chain, Recombinant Wild-Type L Chain with Purified H Chain Native H and L chains are dissociated from BoNT/A (List Biologicals Inc., Campbell, USA) with 2 M urea, reduced with 100 mM DTT and then purified according to established chromatographic procedures. For example, Kozaki et al. (1981, *Japan J. Med. Sci. Biol.* 34, 61) and Maisey et al. (1988, *Eur. J. Biochem.* 177, 683). H chain is combined with an equimolar amount of either native L chain or recombinant wild-type L chain. Reconstitution is carried out by dialyzing the samples against a buffer consisting of 25 mM Tris (pH 8.0), 50 $\mu$M zinc acetate and 150 mM NaCl over 4 days at 4° C. Following dialysis, the association of the recombinant L chain and native H chain to form disulfide linked 150 kDa dichains is monitored by SDS-PAGE and quantified by densitometric scanning. The proportion of dichain molecules formed with the recombinant L chains is lower than that obtained when native L chain is employed. Indeed, only about 30% of the recombinant wild-type or mutant L chain is reconstituted while >90% of the native L chain reassociated with the H chain. In spite of this lower efficiency of reconstitution, sufficient material incorporating the recombinant L chains is easily produced for use in subsequent functional studies.

EXAMPLE 11

Expression of TeTx Fusion Proteins and Purification of Wild-Type L Chain Proteins This Example describes the techniques to produce and purify recombinant L chain fusion proteins encoded by the plasmid constructs described in the previous Example B. *E. coli* clones harboring plasmids PMAL-L are grown to densities of roughly $2\times10^8$ cells/ml ($A_{500\ nm}$~0.5) at 37° C. in L-broth that is made 10 $\mu$g/ml ampicillin and 2 mg/ml glucose. Induction is initiated by the addition of IPTG to a final concentration of 0.3 mM. Cells are harvested 2 hours later by centrifugation at 6000×g for 30 minutes. The resulting pellets are then resuspended in column buffer [10 mM Tris-HCl, 200 mM NaCl, 1 mM ethylene glycol bis (β-aminoethyl ether)-N,N,N',N'-tetraacetic acid, and 1 mM dithiothreitol (DTT) (pH 7.4)] containing 1 mM phenylmethanesulfonyl fluoride (PMSF) and lysed by sonication. After centrifugation, crude extracts are applied to an amylose affinity column (2.5×10 cm, 40 ml of resin).

Following the removal of nonbound proteins by washing with buffer, the bound MBP-L fusion proteins are eluted with column buffer containing 10 mM maltose according to the procedure described by Maina et al., in *Gene* 74, 365 (1988). The isolated fusion proteins are concentrated to 0.5–1 mg/ml using an Amicon CENTRICON. Protein samples are then analyzed by sodium dodecyl sulfate polyacrylamide gel electrophoresis (SDS-PAGE) and Western blotting, using anti-MBP polyclonal and anti-L chain monoclonal antibodies. SDS-PAGE of both cell extracts indicated the presence of an induced protein band ($M_r$~90,000) that is absent from the Coomassie staining pattern of the noninduced cultures. The molecular weight of the protein band is in accordance with that expected from a fusion of MBP and L chain ($M_r$~40,000 and 50,000, respectively). The optimal conditions established for expressing recombinant L chain using the pMAL-c2 vector system are 2 hours of induction with IPTG at 37° C. Neither a longer induction time nor the inclusion of protease inhibitors increased the product yield. Both fusion proteins are soluble in aqueous buffer (up to 0.5 mg/ml) and stable for up to 8 months when stored at −20° C.

After this initial purification step, both MBP-L chain preparations are cleaved at 23° C. for 24 hours with factor X, at an enzyme:protein ratio of 0.5–1:100 (w/w). This cleavage gave complete conversion of the fusion proteins to the respective wild-type L chain with the liberation of MBP, as confirmed by SDS-PAGE. After extensive dialysis against the column buffer to remove maltose, L chain is further purified by reabsorption onto a new affinity column. The desired product from this purification step is found in the column wash fraction. Fractions of the column wash are monitored for $A_{280nm}$ and checked again by SDS-PAGE and Western blotting.

For amino acid sequencing, recombinant wild-type is run on SDS-PAGE and transferred onto a poly(vinytidene difluoride) membrane as described by Tons et al. in *Anal. Biochem.* 179, 50 (1989), with automated Edman degradation performed on a Model 4000 protein sequencer (Chelsea Instruments, London). Microsequencing of the two products revealed four residues identical to those of the N-terminus of native L chain preceded by the 11 amino acids encoded by the multiple cloning site of the vector as depicted in FIG. 1A. Given this success in producing recombinant L chain proteins having the desired structures, we next tested the enzymatic activities of these compositions.

Measurement of the zinc-dependent protease activity of native L chain is employed as an assay for the activity of the recombinant L chain proteins. Two different protein substrates are used in this assay. In the first case, bovine small synaptic vesicles (SSVs) are used. The assay for proteolytic cleavage of the substrate is based on Coomassie staining and Western blotting of protein gels.

Methods of assessing the proteolytic activities of the recombinant L chain proteins and quantifying the in vitro activities of native and recombinant L chains are known and may be used to assess and quantify these recombinant L chains.

EXAMPLE 12

Reassociation of TeTx from Native H Chain and Recombinant L Chain

This example describes a method to prepare TeTx dichains that incorporates either native L chain or recombinant wild-type L chain. Native H chain, purified from TeTx as detailed by Weller et al. in *Eur. J. Biochem.* 182, 649 (1989), is combined with an equimolar amount of either native L chain or recombinant wild-type L. The mixtures are dialyzed against 2 M urea, 20 mM DTT, 1 M NaCl, and 50 mM Tris-HCl (pH 8.4) with stirring for 18 hours and then further dialyzed without agitation against 50 mM Tris-HCl and 600 mM glycine (pH 8.4) for 72 hours. An aliquot (300 μg) is loaded onto an HPLC DEAE column in 25 mM Tris-HCl buffer (pH 8.4) and eluted with an NaCl gradient (0–1 M) in the same buffer. The extent of covalent reconstitution is checked by non-reducing SDS-PAGE and silver staining.

The reassociation of dichain species is confirmed by virtue of the presence of stained high Mr protein bands that comigrated with native TeTx. With respect to recombinant wild-type and mutant L chains, the relative amounts of the dichain species are 55.1 and 56.8%, respectively, as determined by densitometric scanning of the silver-stained gel. Native H chain and L chain gave similar levels of reconstitution. The latter involved interchain disulfide formation as the toxin is converted back to free H chain and L chain upon reduction by DTT.

While this invention has been described with respect to various specific examples and embodiments, it is to be understood that the invention is not limited thereto and that it can be variously practiced with the scope of the following claims.

I claim:

1. A method for treating a gonadotrophin related illness in a mammal, said method comprises the steps of:

(I) administering to the mammal a therapeutically effective amount of an agent, the agent comprises:

(a) an $LH_N$ which comprises (i) a light chain component, an L-chain of a *botulinum* toxin, a butyricum toxin, or a tatani toxin and (ii) a translocation component, an $H_N$ of a *botulinum* toxin, a butyricum toxin, or a tatani toxin; and (b) a targeting component which comprises a gonadotrophin-releasing hormone (GnRH) or GnRH analog, wherein the $LH_N$ is covalently coupled to the GnRH or GnRH analog, and wherein the targeting component selectively binds to a GnRH receptor; and (II) alleviating the gonadotrophin related illness by lowering the level of a gonadotrophin secretion, wherein the gonadotrophin related illness is selected from the group consisting of breast cancer, prostate cancer, pancreatic cancer, and endometrial cancer.

2. The method according to claim 1 wherein the light chain component of the agent decreases the release of a hormone from a cell.

3. The method according to claim 1 wherein the light chain component of the agent is the light chain of *botulinum* toxin type A, B, $C_1$, D, E, F, or G.

4. The method according to claim 1 wherein the light chain component of the agent is the light chain of *botulinum* toxin type A.

5. The method according to claim 1 wherein the translocation component of the agent is the $H_N$ of *botulinum* toxin type A, B, $C_1$, D, E, F, or G.

6. The method according to claim 1 wherein the translocation component of the agent is the $H_N$ of *botulinum* toxin type A.

* * * * *